United States Patent

Sebag et al.

[11] Patent Number: 5,411,742
[45] Date of Patent: May 2, 1995

[54] COMPOSITIONS FOR THE TREATMENT OF ACNE CONTAINING A DERIVATIVE OF SALICYLIC ACID AND DERIVATIVES OF SALICYLIC ACID

[75] Inventors: Henri Sebag; Alain Ribier, both of Paris; Pascal Simon, Vitry-sur-Seine; Laurence Sebillotte, Paris, all of France

[73] Assignee: L'Oreal, Paris, France

[21] Appl. No.: 110,174

[22] Filed: Aug. 23, 1993

[30] Foreign Application Priority Data

Aug. 24, 1992 [FR] France .................. 92 10227

[51] Int. Cl.$^6$ ............................ A61K 9/127
[52] U.S. Cl. .................... 424/450; 424/401; 424/62; 424/63; 428/402.2
[58] Field of Search ............ 424/450, 401, 62, 63; 428/402.2

[56] References Cited

U.S. PATENT DOCUMENTS

| | | | |
|---|---|---|---|
| 4,897,308 | 1/1990 | Vanlabughe | 428/402.2 |
| 5,001,156 | 3/1991 | Philippe et al. | 514/555 |
| 5,019,567 | 5/1991 | Philippe | 514/164 |

Primary Examiner—Gollamudi S. Kishore
Attorney, Agent, or Firm—Cushman Darby & Cushman

[57] ABSTRACT

Composition for the treatment of acne containing a dispersion of vesicles of ionic or non-ionic amphiphilic lipids, the vesicles containing in the lipid phase at least one salicylic acid derivative of formula (I):

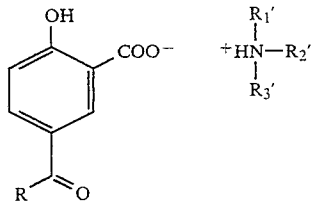

in which R represents a linear or branched $C_{11}$–$C_{17}$ alkyl radical; $R'_1$, $R'_2$, $R'_3$, which are identical or different, represent a $C_1$–$C_{18}$ alkyl or hydroxyalkyl radical, it being possible for one of the radicals $R'_1$, $R'_2$ or $R'_3$ to be a benzyl radical. The derivative of formula (I) serves both as charged lipid and as anti-acne active ingredient. The derivatives of formula (I) in which, when R represents a $C_{13}$–$C_{17}$ alkyl radical, $R'_1$, $R'_2$, $R'_3$, when they are identical, do not represent a hydroxyethyl radical.

15 Claims, No Drawings

COMPOSITIONS FOR THE TREATMENT OF ACNE CONTAINING A DERIVATIVE OF SALICYLIC ACID AND DERIVATIVES OF SALICYLIC ACID

The present invention relates to a composition for the treatment of ache containing a derivative of salicylic acid and special derivatives of salicylic acid which can be used in the said composition.

The aetiopathogenesis of acne, although poorly defined, has its origin in the formation of a characteristic lesion, the comedo. The latter results from the obstruction of the pilosebaceous canal following a diskeratinization of the infundibulum zone of the canal. This obstruction has the major effect of modifying the rheology of the sebum and the physico-chemical characteristics of the medium, such as the pH and the vapor pressure of oxygen. This modification permits the hyperproliferation of the skin resident strains, mainly PROPIONIBACTERIUM AGNES, which is an anaerobic or aerotolerant strain. The bacterial hyperproliferation results in the release, into the medium, of certain proteases or hyaluronidases, of bacterial origin, which cause a lysis of the follicular sac and the release of inflammatory compounds into the dermis, thus triggering an inflammatory type reaction of the organism. While the nature of the inflammatory compounds is at present non determined, there is little doubt concerning their bacterial origin, which explains the high therapeutic success in inflammatory acne of antibacterial compounds both orally and topically.

It has already been proposed to use, as antibacterial agents, in the treatment of acne derivatives of salicylic acid, especially in FR-A 2,581,542 and FR-A 2,607,498. These antibacterial agents are used in the form of emulsions, gels or lotions.

Moreover, it is known that some amphiphilic lipids possess the property of forming mesomorphic phases, whose organizational state is intermediate between the crystalline state and the liquid state and that, among them, some are capable of swelling in the presence of an aqueous solution in order to form a lamellar phase and then, after stirring, to form vesicles dispersed in an aqueous dispersion phase designated by the reference "D". These vesicles are formed by membrane consisting of essentially concentric sheets composed of one or more multimolecular, preferably bimolecular, layers, the various lipid layers being separated by a layer of aqueous phase and encapsulating an encapsulated aqueous phase designated by the reference "E". The amphiphilic lipids capable of forming vesicles are, in a known manner, ionic amphiphilic lipids and/or non-ionic amphiphilic lipids.

These vesicles may be prepared by numerous processes. According to a first process, which is for example described by BANGHAM et al. (J. Mol. Bio., 13, 1965 pages 238 to 262), a lipid phase is dissolved in a volatile solvent, a thin film of lipid phase is formed on the sides of a bottle by evaporation of the solvent, the phase to be encapsulated is introduced onto the lipid film and the mixture is mechanically stirred until the dispersion of vesicles having the desired size is obtained; an aqueous dispersion of vesicles encapsulating an aqueous phase E is thus obtained, the encapsulated aqueous phase E and the aqueous dispersion phase D being identical. According to a second so-called lipid co-melting process, described for example in FR-A-2,315,991, the lipid phase is prepared by mixing the amphiphilic lipid(s) and optional additives, at a temperature where the mixture is melted, if the mixture is not liquid at room temperature; a lamellar phase is formed by introducing the aqueous phase to be encapsulated E; then the lamellar phase is dispersed in the form of vesicles by means of an ultra-dispersing device, a homogenizer or ultrasound, in an aqueous dispersion phase D. In a variant of this process, the formation of the lamellar phase does not constitute a separate stage of the process. The vesicles obtained by these two processes are generally of the "multisheet" type. In order to obtain vesicles of the "monosheet" type, a process may be used which consists in solubilizing the lipid mixture with octyl glucoside and in forming the vesicles according to the teaching of FR-A-2,543,018. This enumeration of processes is not at all limiting and the invention is applicable regardless of the process for the manufacture of vesicles in the form of a dispersion in an aqueous phase.

It is known to introduce into the lipid phase additives intended to improve the physiochemical stability (flocculation, melting), to decrease the permeability of the lipid membrane to the encapsulated substances, and to increase the encapsulation level.

The additives intended to improve the physiochemical stability are, in a known manner, sterols and charged lipids. The role of sterols, in particular cholesterol, is to extend the zone of stability of the vesicles over a wider temperature range and to decrease their permeability to the substances encapsulated in the aqueous encapsulation phase.

The role of charged lipids such as dicetyl or dimyristryl phosphate, cholesteryl phosphate, phosphatidic acid, long-chain amines or quaternary ammonium is to improve the stability of the vesicles by preventing their flocculation and, consequently, their melting, even in the presence of electrolytes, and to allow an increase in the level of encapsulation of watersoluble substances by increasing the thickness of the aqueous layers separating the lipid sheets constituting the membrane. It is known to add to the lipid phase several of these additives, in particular at least one sterol typeadditive and at least one charged lipid type additive.

It is moreover also known to incorporate into the lipid phase a cosmetic and/or dermopharmaceutical active ingredient. The active ingredients which can be used must be fat-soluble and must not destroy the physiochemical stability of the vesicles, must not increase in a disruptive manner their permeability to the encapsulated substances, and must not decrease their encapsulation level.

Some compounds, for example cholesterol, improve the physico-chemical stability and the encapsulation level and also have a cosmetic and/or dermopharmaceutical activity. Compounds which have a cosmetic and/or dermopharmaceutical activity and which, furthermore, improve the stability of the vesicles and their encapsulation level are therefore preferably used.

According to the present invention, it has been discovered that some derivatives of salicylic acid, which have an anti-acne activity, may also be incorporated as anionic charged lipids into the lipid phase forming the membrane of vesicles of amphiphilic lipids. Vesicles which have a high physiochemical stability, an adequate permeability, a high encapsulation level and which also have an anti-acne activity may therefore be thus obtained.

The subject of the invention is therefore a composition for the treatment of acne by topical application containing a dispersion, in an aqueous phase D, of vesicles of amphiphilic lipid(s) consisting of a lipid phase membrane encapsulating an aqueous phase E, the lipid phase containing as additive a charged lipid characterized by the fact that the lipid phase contains at least one salicylic acid derivative of formula:

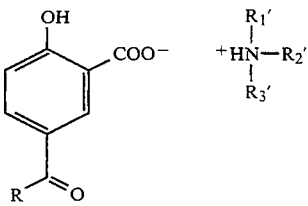   I in which formula (I):

R represents a linear or branched $C_{11}$-$C_{17}$ alkyl radical, preferably a linear $C_{11}$ alkyl radical, $R'_1$, $R'_2$ and $R'_3$, which are identical or different, represent a $C_1$-$C_{18}$ alkyl or hydroxyalkyl radical, it being possible for one of the radicals $R'_1$, $R'_2$ or $R'_3$ to be a benzyl radical.

The lipid phase preferably contains 3% to 10% by weight of compound of formula (I). For quantities less than 3%, the vesicles have no anti-acne activity and for quantities greater than 10%, the physiochemical stability of the vesicles obtained begins to decrease.

The preferred salicylic acid derivative of formula (I) is N, N-dimethyl-N-(2-hydroxyethyl)ammonium 5-n-dodecanoylsalicylate.

It was not obvious that the incorporation, in a quantity ranging up to 10% of salicylic acid derivatives of formula (I) into the lipid phase forming the membrane of the vesicles would make it possible to obtain vesicles having a high physico-chemical stability and a high encapsulation level. Indeed, tests have shown that it is not possible to introduce more than 4% of 5-dodecanoylsalicylic acid into the lipid phase of amphiphilic lipids. Indeed, for higher proportions, this derivative precipitates in the lipid phase. The incorporation of hexadecylpyridinium 5-octanoylsalicylate or hexadecyltrimethylammonium 5-dodecanoylsalicylate does not improve the physiochemical stability of the vesicles and it is therefore necessary to introduce into the lipid phase a conventional charged lipid. The trimethyl-β-hydroxyethylammonium 5-dodecylsalicylate incorporated at a level ranging up to 10% by weight makes it possible to obtain vesicles having a high physico-chemical stability but the encapsulation capacity of the vesicles decreases by about 50% relative to the encapsulation capacity of the vesicles prepared with the same lipids but not containing the said dodecyl salicylate.

On the other hand, it was observed that, in a determined lipid phase containing dicetyl phosphate which is frequently used as charged lipid, all the dicetyl phosphate could be replaced with a salicylic acid derivative of formula (I) according to the invention without practically modifying the physico-chemical stability of the vesicles obtained and their encapsulation level.

According to the invention, the constituent lipid phase of the membranes of the vesicles of the dispersion comprises, in a known manner, at least one amphiphilic lipid chosen from the group consisting of:

A/ the non-ionic lipids defined below:

(1) the linear or branched glycerol derivatives of formula:

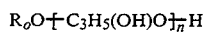

in which formula:

represents the following structures taken together or separately:

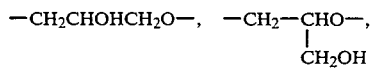

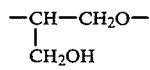

n is a mean statistical value between 1 and 6 or alternatively n is a real value equal to 1 or 2, in which case $C_3H_5(OH)O$ represents the structure

$R_0$ represents:

(a) a saturated or unsaturated linear or branched aliphatic chain containing 12 to 30 carbon atoms; or hydrocarbon radicals of lanolin alcohols; or long-chain alpha-diol residues;

(b) a residue $R_1CO$, where $R_1$ is a linear or branched $C_{11}$-$C_{29}$ aliphatic radical;

(c) a residue:

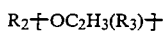

where $R_2$ may have the meaning (a) or (b) given for $R_0$;

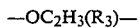

represents the following structures, taken together or separately,

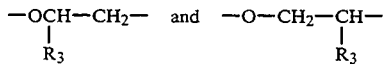

where $R_3$ has the meaning (a) given for $R_0$;

(2) linear or branched polyglycerol ethers containing two fatty chains;

(3) fatty chain diols;

(4) oxyethylenated or non-oxyethylenated fatty alcohols, sterols such as for example cholesterol and phytosterols, oxyethylenated or non-oxyethylenated;

(5) oxyethylenated or non-oxyethylenated polyol ethers and esters, it being possible for the chain of ethylene oxides to be linear or cyclic;

(6) glycolipids or natural or synthetic origin, mono- or polysaccharide ethers and esters and especially glucose ethers and esters;

(7) the hydroxyamides described in French Patent No. 2,588,256 and represented by the formula:

$$R_4-CHOH-CH-COA$$
$$|$$
$$R_5-CONH$$

in which formula:

$R_4$ designates a $C_7-C_{21}$ alkyl or alkenyl radical;

$R_5$ designates a saturated or unsaturated $C_7-C_{31}$ hydrocarbon radical;

COA designates a group chosen from the following two groups:

a residue $$CON-B$$
$$|$$
$$R_6$$

where:

B is an alkyl radical derived from mono- or polyhydroxylated primary or secondary amines; and $R_6$ designates a hydrogen atom or a methyl, ethyl or hydroxyethyl radical; and a residue -COOZ where Z represents a $C_3-C_7$ polyol residue;

(8) natural or synthetic ceramides;

(9) dihydroxyalkylamines, oxyethylenated fatty amines;

(10) the glycerol derivatives described in Patent Application WO-A 92/08685 and corresponding to the formula:

$$CH_2-CH-CH_2-O-\left[CH_2-CH-O\right]_n-H$$
$$|\quad\ |\qquad\qquad\quad\ |$$
$$OH\ \ OH\qquad\qquad\ R_7$$

in which formula $R_7$ represents a linear $C_{14}-C_{18}$ alkyl radical or a group $-CH_2A$ in which A is $OR_{14}$, $R_{14}$ representing a linear $C_{10}-C_{18}$, and preferably $C_{16}$, alkyl radical, and n represents a mean statistical value greater than 1 and not more than 3 and, in addition, when $R_7=-CH_2A$, n may also represent a real value (non statistical) equal to 2.

(11) Glucose esters of formula:

$$\begin{array}{c}O\\ \|\\ OCR_{15}\\ H\ |\\ \ \ CH_2\quad\ O\\ HO\diagdown\quad\diagup H\diagdown\\ \quad\ \ H\\ HO\diagup\diagdown\quad\diagup\\ \qquad\quad\ OH\quad H,\ OH\\ \qquad\ H\end{array}$$

in which formula $R_{15}$ represents a saturated or unsaturated linear $C_9-C_{17}$ hydrocarbon chain, which are described in EP-A 485251.

B) The ionic amphiphilic lipids defined below:

(1) anionic amphiphilic lipids such as:

natural phospholipids, especially egg or soya bean lecithin or sphingomyelin, phospholipids modified chemically or enzymatically, especially hydrogenated lecithin, and synthetic phospholipids, especially dipalmitoylphosphatidylcholine;

anionic compounds such as those described in French Patent No. 2,588,256 and represented by the formula:

$$R_8-CHOH-CH-COOM_1$$
$$|$$
$$R_9CONH$$

in which formula:

$R_8$ represents a $C_7-C_{21}$ alkyl or alkenyl radical;

$R_9$ represents a saturated or unsaturated $C_7-C_{31}$ hydrocarbon radical, and $M_1$ represents H, Na, K, $NH_4$, or a substituted ammonium ion derived from an amine, (2) anionic compounds such as phosphoric esters of fatty alcohols, for example dicetyl phosphate and dimyristyl phosphate in the form of acids or alkali metal salts; heptyl nonyl benzene sulphonic acid; acid cholesterol sulphate and its alkali metal salts; acid cholesterol phosphate and its alkali metal salts; lysolecithins; alkyl sulphates, for example sodium cetyl sulphate; gangliosides;

(3) cationic amphiphilic lipids such as:

quaternary ammonium-derived cationic compounds corresponding to the formula:

$$\begin{array}{c}R_{10}\diagdown\ +\ \diagup R_{12}\\ N\qquad X^-\\ \diagup\ \ \diagdown\\ R_{11}\qquad R_{13}\end{array}$$

in which formula:

$R_{10}$ and $R_{11}$, which are identical or different, represent $C_{12}-C_{20}$ alkyl radicals and $R_{12}$ and $R_{13}$, which are identical or different, $C_1-C_4$ alkyl radicals;

long chain amines and their quaternary ammonium derivatives, esters of long-chain amino alcohols and their salts and quaternary ammonium derivatives;

polymerizable lipids such as those described by Ringsdorf et al. in "Angewandte Chemie", Vol. 27, No. 1, January 1988, pages 129 and 137.

The amphiphilic lipid(s) used preferably represents (represent) 0.5 to 25% by weight relative to the total weight of the composition.

As explained above, the lipid phase according to the invention may also contain, in a known manner, sterols such as phytosterols, and more particularly cholesterol. The lipid phase may also optionally contain charged lipids and/or fat-soluble active ingredients other than the salicylic acid derivative of formula (I) which are fat-soluble such as retinoic acid, tocopherols, linoleic acid.

In a known manner, the encapsulated aqueous phase E and/or the aqueous dispersion phase D may contain water-soluble cosmetic and/or dermopharmaceutical active ingredients such as glycerol, sorbitol, erythrulose or antibiotics.

As cosmetic and/or dermopharmaceutical active ingredients, there may be mentioned antioxidants, anti-free radical agents, moisturizing agents, tanning-promoting agents, depigmenting agents, skin coloring B agents, fat-regulating agents, anti-aging agents, anti-UV agents, keratolytic agents, emollient agents, antiinflammatory agents, refreshing agents, cicatrizing agents, vascular protectors, antibacterial agents, antifungal agents. A list of such active ingredients can be found in Application WO-A-92/08685.

The vesicles advantageously have a mean diameter of between 100 and 500 mm.

The aqueous-dispersion phase D according to the invention may, in a known manner, consist of water or a mixture of water and at least one water-miscible solvent such as $C_1$–$C_7$ alcohols and $C_1$–$C_5$ alkyl polyols.

The aqueous dispersion phase D may contain, in a known manner, a dispersion of droplets of a water-immiscible liquid, which the vesicles stabilize. Consequently, in the presence of vesicles of ionic amphiphilic lipids and/or non-ionic amphiphilic lipids, it is not necessary to introduce a customary emulsifying agent.

According to the present invention, the water-immiscible liquid, which maybe present in the form of a dispersion in the aqueous dispersion phase D, consists of any water-immiscible liquid which is generally known to be capable of being introduced into the aqueous phase of the dispersion of vesicles of ionic or non-ionic lipids; it may especially be chosen from the group consisting of:

- an animal or vegetable oil consisting of esters of fatty acid and polyols, in particular liquid triglycerides, for example sunflower, maize, soya bean, cucurbit, grape seed, jojoba, sesame or hazelnut oils, fish oils, glycerol tricaprocaprylate or a vegetable or animal oil of formula $R_{15}COOR_{16}$, in which formula $R_{15}$ represents a higher fatty acid residue containing 7 to 19 carbon atoms and $R_{16}$ represents a branched hydrocarbon chain containing 3 to 20 carbon atoms, for example purcellin oil;
- natural or synthetic essential oils such as for example eucalyptus, lavandin, lavender, vetiver, litsea cubeba, lemon, sandalwood, rosemary, camomile, savory, nutmeg, cinnamon, hyssop, caraway, orange, geraniol and cade oils;
- hydrocarbons such as hexadecane and paraffin oil;
- halogenated hydrocarbons, especially fluorocarbons such as fluoroamines, for example perfluorotributylamine, fluorinated hydrocarbons, for example perfluorodecahydronaphthalene, fluoroesters and fluoethers;
- silicones, for example polysiloxanes, polydimethylsiloxanes and fluorosilicones;
- esters of inorganic acid and an alcohol;
- ethers and polyethers.

The water-immiscible liquid may contain one or more lipophilic active ingredients.

The aqueous phase D of the dispersion of vesicles according to the invention may also contain, in a known manner, formulation additives essentially necessary for the formulation of the compositions in the form of lotion, cream or serum. These additives are in particular chosen from the group consisting of gelling agents, polymers, preservatives, colorants, opacifying agents, pH-regulating agents, perfumes. Among the gelling agents which can be used, there may be mentioned cellulose derivatives such as hydroxyethylcellulose; algal derivatives such as satia gum; natural gums such as tragacanth, and synthetic polymers, in particular the polycarboxyvinylic acid mixtures marketed under the tradename "CARBOPOL" by the company GOODRICH.

The subject of the invention is also the salicylic acid derivatives of formula (I) which are new. They are the compounds of formula (I):

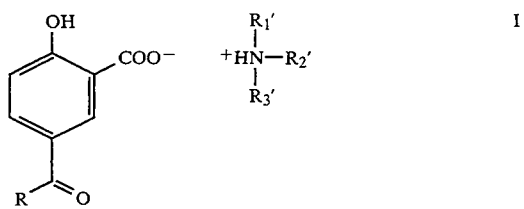

in which:
R represents a linear or branched $C_{11}$–$C_{17}$ alkyl radical, preferably a linear $C_{11}$ alkyl radical,
$R'_1$, $R'_2$, $R'_3$, which are identical or different, represent a $C_1$ to $C_{18}$ alkyl or hydroxyalkyl radical, it being possible for one of the $R'_1$, $R'_2$ or $R'_3$ radicals to be a benzyl radical, provided that when R represents a $C_{13}$ to C7 alkyl radical, $R'_{19}$, $R'_2$ and $R'_3$, when they are identical, do not represent a hydroxyethyl radical.

These compounds are advantageous since, as explained above, when they are introduced into the lipid phase of the membrane of vesicles, they serve both as charged lipids and as anti-acne active ingredients.

The compounds of formula (I) are prepared by salification of the corresponding 5-acylsalicylic acid in the presence of an amine solubilized in an alcoholic medium such as methanol, ethanol or isopropanol. The corresponding 5-acylsalicylic acid is obtained by a FRIEDEL-CRAFTS type acylation reaction between an acid chloride and the methyl ester of salicylic acid in the presence of a catalyst such as anhydrous aluminum chloride. Such reactions are described particularly by OLAH, "FRIEDEL-CRAFTS and Related Reactions", Interscience Publishers, New York, 1963-1964 or by GORE, Chem. Rev. 55, 229–281 (1955).

The reaction scheme is the following:

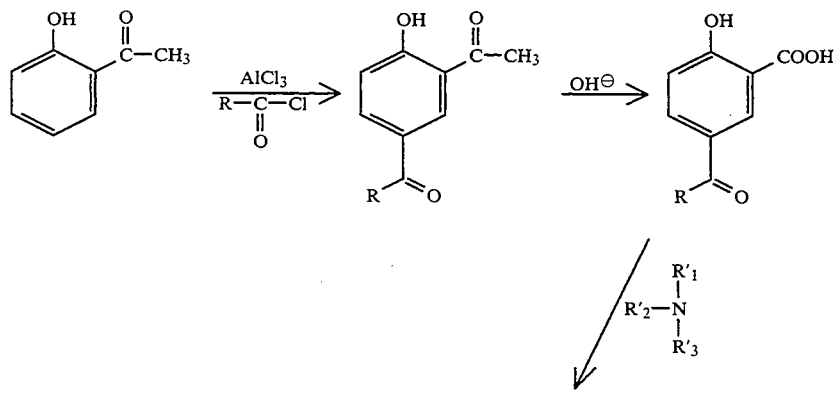

-continued

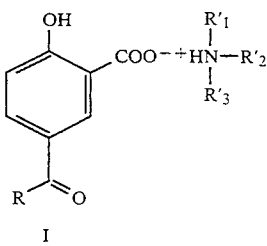

The examples given below, by way of illustration with no limitation being implied, will make it possible to understand the invention more clearly. Examples 1 to 4 below relate to the preparation of salicylic acid derivatives of formula (I) according to the invention.

EXAMPLE 1

Preparation of N,N,N-tri(2-hydroxypropyl)ammonium 5-n-dodecanoylsalicylate.

Into a beaker, are added, with stirring, 11.4 g (0.06 mole) of triisopropanolamine in 100 ml of isopropanol. The reaction medium is stirred and cooled to between 5° and 10° C. 19.2 g (0.06 mole) of 5-n-dodecanoylsalicylic acid are then added. The mixture is stirred for 30 min at room temperature and then the clear mixture is filtered. The filtrate is evaporated to dryness. An oil is obtained which crystallizes at room temperature. It is filtered on sintered glass. The white powder obtained is dried under vacuum over phosphoric anhydride. 29.1 g of product are obtained, equivalent to a yield of 95%.

The characteristics are the following: Acid value: 2.02–2.04 meq/g (theory: 1.96) Base value: 1.93–1.94 meq/g (theory: 1.96) Kraft point: 50° C.

EXAMPLE 2

Preparation of N-hydroxy-tert-butylammonium 5-n-dodecanoylsalicylate.

The compound is prepared according to the same procedure as in Example 1, using:
- 6.6 g (0.075 mole) of 2-amino-2-methylpropanol
- 24 g (0.075 mole) of 5-n-dodecanoylsalicylic acid 27.6 g of a white powder are obtained, equivalent to a yield of 90%.

The analysis of the product obtained is the following: Acid value: 2.58 meq/g (theory: 2.44) Base value: 2.36–2.38meq/g (theory: 2.44) Kraft point: 47° C.

EXAMPLE 3

Preparation of N,N-dimethyl-N-(2-hydroxyethyl)ammonium 5-n-dodecanoylsalicylate.

The compound is prepared according to the same procedure as in Example 1, using:
- 1.6 ml (0.0156 mole) of N,N-dimethylethanolamine
- 5 g (0.0156 mole) of 5-n-dodecanoylsalicylic acid 6.1 g of product are obtained in the form of a white powder, equivalent to a yield of 95%.

The melting point of the product obtained is 58° C. The elemental analysis is the following:

|   | C | H | N | O |
|---|---|---|---|---|
| % calculated | 67.48 | 9.53 | 3.42 | 19.56 |
| % found | 67.44 | 9.60 | 3.34 | 19.51 |

The $^{13}$C NMR spectrum is in conformity with the expected structure.

EXAMPLE 4

Preparation of triethylammonium 5-n-dodecanoylsalicylate.

The compound is prepared according to the same procedure as in Example 1, using:
- 6 g (0.06 mole) of triethylamine
- 19.2 g (0.06 mole) of 5-n-dodecanoylsalicylic acid 22.7 g of a white powder are obtained, equivalent to a yield of 90%.

The characteristics of the product obtained are the following: Acid value: 2.48–2.49 meq/g (theory: 2.38) Base value: 2.26 meq/g (theory: 2.38)

Examples 5 to 7 given below are examples of formulation of compositions containing a dispersion in aqueous phase of vesicles containing, in the lipid phase of the membrane, salicylic acid derivatives of formula (I).

EXAMPLE 5

Skin Care Cream

The mixture of the following products is produced by melting at the temperature of 110° C.: Amphiphilic compound of formula:

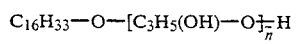

formula where n is a mean statistical value equal to 3 and where

represents the structures, taken together or separately:

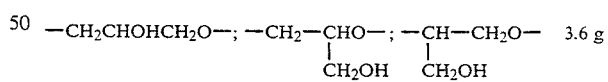

| | |
|---|---|
| Cholesterol | 3.6 g |
| Compound of Example 3 | 0.8 g |

Then the temperature of the molten mixture is adjusted to 90° C. 20 g of water containing 3 g of glycerin are then added and the mixture obtained is homogenized at the temperature of 90° C. 37.27 g of water are then added at the temperature of 70° C., and the mixture obtained is homogenized by means of the ultra-dispersing device "VIRTIS" for 4 minutes at the speed of 40,000 rpm. A dispersion of lipid vesicles is thus obtained.

There are then added 5 g of water containing:
0.15 g of diazolidinyl urea sold under the name "GERMAL II" by the company "SUTTON", and 0.05 g of dipotassium salt of ethylenediaminotetraacetic acid.

There are then added:

10 g of decamethylcyclopentasiloxane sold under the name "SILBIONE Huile 700 45 V5" by the company "RHONE POULENC"

0.5 g of dimethicone sold under the name "SILBIONE 747 V 300" by the company "RHONE POULENC"

0.01 g of propyl para-oxybenzoate and the mixture is homogenized by means of the ultra-dispersing device "VIRTIS" for 4 minutes at 40,000 rpm.

There are finally added:

0.42 g of cross-linked polyacrylic acid sold under the name "CARBOPOL 940" by the company "GOODRICH"

0.2 g of methyl paraoxybenzoate 15 g of water and 0.4 g of triethanolamine

A thick white cream is thus obtained. After application of this cream in the evening and in the morning in an amount of 0.3 g on the face of a subject having a skin with acne, a sharp regression of the acne is observed after 3 weeks.

EXAMPLE 6

Skin Care Cream

The following products are dissolved in a round-bottom flask:

| | |
|---|---|
| hydrogenated soya bean lecithin sold under the name "LECINOL S 10" by the company "NIKKO" | 2.4 g |
| Cholesterol | 1.2 g |
| Compound of Example 3 | 0.4 g | in 50 ml of a chloroform/methanol (1/1) solvent mixture. The solvent is then evaporated by means of a rotary evaporator. The mixture is then hydrated by means of 10 g of Water at the temperature of 90° C. and homogenized by means of a spatula and then transferred into a beaker. 43.56 g of water are then added at the temperature of 70° C. The mixture is homogenized by means of an ultra-dispersing device "VIRTIS" for 4 minutes at the temperature of 70° C. and then adjusted to room temperature. There are then added 5 g of water containing 0.3 g of imidazolidinyl urea sold under the name "GERMAL 115" by the company "SUTTON" and 0.1 g of a mixture of methylchloroisothiazolinone and methylisothiazolinone sold under the name "KATHON CG" by the company "ROHM and HASS". 15 g of macadamia oil are then added and the mixture is homogenized by means of the dispersing device Virtis for 4 minutes at 40,000 rpm.

There are finally added:

0.42 g of cross-linked polyacrylic acid sold under the name "CARBOPOL 940" by the company "GOODRICH"

0.2 g of methyl paraoxybenzoate 15 g of water and 0.42 g of triethanolamine

A thick white cream is thus obtained. After application of this cream in the evening and in the morning in an amount of 0.2 g on the face of a subject having a skin with acne, a sharp regression of the acne is observed after 3 weeks.

EXAMPLE 7

Skin Care Cream

Using the procedure of Example 5, a composition having the following formulation is prepared:

| | |
|---|---|
| Amphilic compound of Example 5 | 2.7 g |
| Cholesterol | 2.7 g |
| N,N-dimethyl-N-(2-hydroxyethyl)ammonium 5-dodecanoylsalicylate (compound of Example 3) | 0.6 g |
| Glycerin | 3 g |
| Disodium salt of ethylenediaminotetraacetic acid | 0.15 g |
| Sunflower oil | 4 g |
| Butylated hydroxytoluene | 0.05 g |
| Silicone oil sold under the name "Volatil silicone 7158" by the company "UNION CARBIDE" | 3 g |
| Preservatives qs | |
| Distilled water qs | 100 g |
| Cross-linked polyacrylic acid sold under the name "CARBOPOL 980" by the company "GOODRICH" | 0.8 g |
| Triethanolamine | 0.8 g |

A thick white cream is thus obtained. After application of this cream in the evening and in the morning in an amount of 0.2 g on the face of a subject having a skin with acne, a sharp regression of the acne is observed after 3 weeks.

EXAMPLE 8

Skin Care Cream

The mixture of the following products is produced by melting at the temperature of 110° C.: Amphiphilic compound of formula:

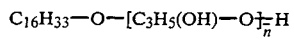

formula where n is a mean statistical value equal to 3 and where

represents the structures, taken together or separately:

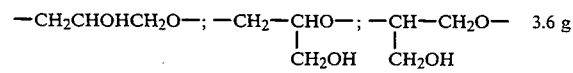 3.6 g

| | |
|---|---|
| Cholesterol | 3.6 g |
| Compound of Example 1 | 0.8 g |

Then the temperature of the molten mixture is adjusted to 90° C. 20 g of water containing 3 g of glycerin are then added and the mixture obtained is homogenized at the temperature of 90° C. 37.27 g of water are then added at the temperature of 70° C., and the mixture obtained is homogenized by means of the ultra-dispersing device "VIRTIS" for 4 minutes at the speed of 40,000 rpm. A dispersion of lipid vesicles is thus obtained.

There are then added 5 g of water containing:

0.15 g of diazolidinyl urea sold under the name "GERMAL II" by the company "SUTTON", and 0.05 g of dipotassium salt of ethylenediaminotetraacetic acid.

There are then added:

10 g of decamethylcyclopentasiloxane sold under the name "SILBIONE Huile 700 45 V5" by the company "RHONE POULENC"

0.5 g of dimethicone sold under the name "SILBIONE 747 V 300" by the company "RHONE POULENC"

0.01 g of propyl para-oxybenzoate and the mixture is homogenized by means of the ultra-dispersing device "VIRTIS" for 4 minutes at 40,000 rpm.

There are finally added:

0.42 g of cross-linked polyacrylic acid sold under the name "CARBOPOL 940" by the company "GOODRICH"

0.2 g of methyl paraoxybenzoate 15 g of water and 0.4 g of triethanolamine

A thick white cream is thus obtained. After application of this cream in the evening and in the morning in an amount of 0.3 g on the face of a subject having a skin with acne, a sharp regression of the acne is observed after 3 weeks.

EXAMPLE 9

Skin Care Cream

The mixture of the following products is produced by melting at the temperature of 110° C.: Amphiphilic compound of formula:

$$C_{16}H_{33}-O-[C_3H_5(OH)-O]_{\overline{n}}H$$

formula where n is a mean statistical value equal to 3 and where $$-C_3H_5(OH)-O-$$

represents the structures, taken together or separately:

$$-CH_2CHOHCH_2O-; \quad -CH_2-\underset{\underset{CH_2OH}{|}}{CHO}-; \quad -\underset{\underset{CH_2OH}{|}}{CH}-CH_2O- \quad 3.6 \text{ g}$$

Cholesterol    3.6 g

Compound of Example 4    0.8 g

Then the temperature of the molten mixture is adjusted to 90° C. 20 g of water containing 3 g of glycerin are then added and the mixture obtained is homogenized at the temperature of 90° C. 37.27 g of water are then added at the temperature of 70° C., and the mixture obtained is homogenized by means of the ultra-dispersing device "VIRTIS" for 4 minutes at the speed of 40,000 rpm. A dispersion of lipid vesicles is thus obtained.

There are then added 5 g of water containing:

0.15 g of diazolidinyl urea sold under the name "GERMAL II" by the company "SUTTON", and 0.05 g of dipotassium salt of ethylenediaminotetraacetic acid.

There are then added:

10 g of decamethylcyclopentasiloxane sold under the name "SILBIONE Huile 700 45 V5" by the company "RHONE POULENC"

0.5 g of dimethicone sold under the name "SILBIONE 747 V 300" by the company "RHONE POULENC"

0.01 g of propyl para-oxybenzoate and the mixture is homogenized by means of the ultra-dispersing device "VIRTIS" for 4 minutes at 40,000 rpm.

There are finally added:

0.42 g of cross-linked polyacrylic acid sold under the name "CARBOPOL 940" by the company "GOODRICH"

0.2 g of methyl paraoxybenzoate 15 g of water and 0.4 g of triethanolamine

A thick white cream is thus obtained. After application of this cream in the evening and in the morning in an amount of 0.3 g on the face of a subject having a skin with acne, a sharp regression of the acne is observed after 3 weeks.

We claim:

1. A composition for the treatment of acne by topical application to the skin, said composition comprising a dispersion of amphiphilic lipidic vesicles in an aqueous phase, said amphiphilic lipidic vesicles encapsulating an aqueous phase; the lipidic phase of said amphiphilic lipidic vesicles comprising an amphiphilic lipid and a charged lipid, said charged lipid is a salicylic acid derivative having the formula

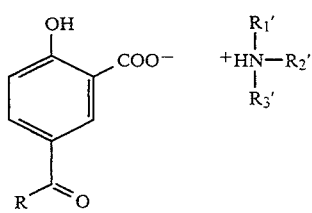

wherein

R represents a linear or branched $C_{11}$-$C_{17}$ alkyl, $R'_1$, $R'_2$ and $R'_3$, each independently, represent $C_1$-$C_{18}$ alkyl or hydroxyalkyl, with one of R, $R_2$ and $R_3$ optionally being benzyl.

2. The composition of claim 1 wherein said salicylic acid derivative is N,N-dimethyl-N-(2-hydroxyethyl) ammonium 5-N-dodecanoyl salicylate.

3. The composition of claim 1 wherein said lipidic phase contains 3 to 10 weight percent of said salicylic acid derivative.

4. The composition of claim 1 wherein said amphiphilic lipid is a nonionic lipid selected from the group consisting of (1) a linear or branched glycerol derivative having the formula, $R_0O+C_3H_5(OH)O]_{\overline{n}}H$ wherein $-C_3H_5(OH)O-$, jointly or separately, represents $$-CH_2CHOHCH_2O-, \quad -CH_2-\underset{\underset{CH_2OH}{|}}{CHO}- \quad \text{or}$$

$$-\underset{\underset{CH_2OH}{|}}{CH}CH_2O-;$$

n has a mean statistical value ranging from 1 to 6, or alternatively n is a real value equal to 1 or 2 in which case $-C_3H_5(OH)O-$ represents $-CH_2CHOH-CH_2O-$; $R_0$ represents (a) a saturated or unsaturated linear or branched $C_{12}$-$C_{30}$ aliphatic chain, (b) a hydrocarbon radical of lanolin alcohol, (c) a long chain alpha-diol residue, (d) a $R_1CO$ residue wherein $R_1$ is a linear or branched $C_{11}$-$C_{29}$ aliphatic radical, (e) a R₂—[—OC₂H₃(R₃)—]—residue wherein R₂ has the meaning (a)–(e) given for R₀ and wherein —OC₂H₃(R₃)— represents, jointly or separately,

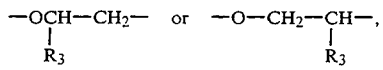

wherein R₃ represents the meaning (a)–(c) given for R₀;
(2) a linear or branched polyglycerol ether having two fatty chains;
(3) a fatty chain diol;
(4) an oxyethylenated or non-oxyethylenated fatty alcohol;
(5) an oxyethylenated or non-oxyethylenated sterol;
(6) an oxyethylenated or non-oxyethylenated polyol ether or ester wherein the ethylene oxide chain is linear or cyclic;
(7) a natural or synthetic glycolipid;
(8) a mono- or poly saccharide ether or ester;
(9) a hydroxyamide having the formula

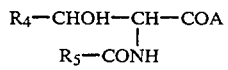

wherein
R₄ represents alkyl or alkenyl having 7 to 21 carbon atoms,
R₅ represents a saturated or unsaturated hydrocarbon radical having 7 to 31 carbon atoms,
COA represents a member selected from the group consisting of
(i)

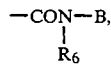

wherein B is a radical derived from a mono- or polyhydroxylated primary or secondary amine, and R₆ is hydrogen, methyl, ethyl or hydroxyethyl, and
(ii) —COOZ wherein Z represents a polyol having 3–7 carbon atoms;
(10) a natural or synthetic ceramide;
(11) a dihydroxyalkyl amine;
(12) an oxyethylenated fatty amine;
(13) a glycerol derivative having the formula

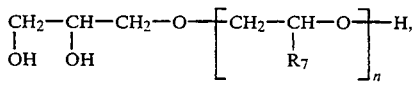

wherein
R₇ represent linear C₁₄–C₁₈ alkyl or —CH₂A wherein A represents OR14 wherein R14 represents linear C10–C18 alkyl, and n represent a mean statistical value greater than 1 and not more than 3, and, additionally, when R₇ is —CH₂A, n can also represent a real value equal to 2; and
(14) a glucose ester having the formula

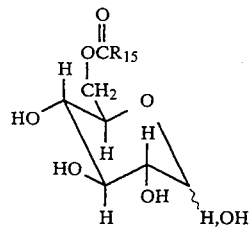

wherein
R₁₅ represents a saturated or unsaturated linear or C₉–C₁₇ hydrocarbon chain.
5. The composition of claim 1 wherein said amphiphilic lipid is an ionic lipid selected from the group consisting of:
(1) an anionic amphiphilic lipid selected from the group consisting of
(i) a natural phospholipid,
(ii) a phospholipid modified chemically or enzymatically,
(2) an anionic compound having the formula

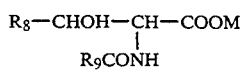

wherein
R₈ represents an alkyl or alkenyl having 7 to 21 carbon atoms,
R₉ represents a saturated or unsaturated hydrocarbon radical having 7 to 31 carbon atoms, and
M₁ represents H, Na, K, NH₄ or a substituted ammonium ion derived from an amine;
(3) an anionic compound selected from the group consisting of
(i') a phosphoric ester of a fatty alcohol,
(ii') heptyl nonyl benzene sulphonic acid,
(iii') acid cholesterol sulphate or an alkali metal salt thereof,
(iv') acid cholesterol phosphate or an alkali metal salt thereof,
(v') a lysolecithin,
(vi') an alkyl sulphate and
(vii') a ganglioside; and
(4) a cationic amphiphilic lipid selected from the group consisting of
(i'') a quaternary ammonium derived cationic compound having the formula

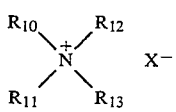

wherein
R₁₀ and R₁₁, each independently, represent a C₁₂–C₂₀ alkyl radical and
R₁₂ and R₁₃, each independently, represent a C₁–C₄ alkyl radical;
(ii'') a long chain amine or a quaternary ammonium derivative thereof; and
(iii'') an ester of a long chain amino alcohol or a salt or quaternary ammonium derivative thereof.
6. The composition of claim 1 wherein said amphiphilic lipid is present in an amount ranging from 0.5 to 25 percent by weight based on the total weight of said composition.

7. The composition of claim 1 wherein said lipidic phase contains a sterol.

8. The composition of claim 7 wherein said sterol is cholesterol.

9. The composition of claim 1 wherein said lipidic phase also contains another charged lipid selected from the group consisting of dicetyl phosphate, dimyristryl phosphate, cholesteryl phosphate, phosphatidic acid and a long chain amine or quaternary ammonium derivative thereof.

10. The composition of claim 1 wherein said lipidic phase also contains a fat soluble active ingredient selected from the group consisting of retinoic acid, a tocopherol and linoleic acid.

11. The composition of claim 1 wherein said aqueous phase encapsulated in said amphiphilic lipidic vesicles further contains an ingredient selected from the group consisting of an antibiotic agent, an antioxidant, a moisturizing agent, a tanning-promoting agent, a depigmenting agent, a skin coloring agent, a fat-regulating agent, an emollient agent, an anti-inflammatory agent, a cicatrizing agent, and an antifungal agent.

12. The composition of claim 1 wherein said amphiphilic lipidic vesicles have a mean diameter ranging form 100 to 500 nm.

13. The composition of claim 1 wherein said aqueous phase in which said amphiphilic lipidic vesicles are dispersed comprises water or a mixture of water and at least one water-miscible solvent selected from the group consisting of a $C_1$–$C_7$ alcohol and a $C_1$–$C_5$ alkyl polyol.

14. The composition of claim 1 wherein said aqueous phase in which said amphiphilic lipidic vesicles are dispersed also contains a dispersion of water-immiscible liquid droplets of a member selected from the group consisting of
  (a) an animal or vegetable oil selected from the group consisting of sunflower oil, maize oil, soya bean oil, cucurbit oil, grape seed oil, jojoba oil, sesame oil, hazelnut oil, fish oil, glycerol tricaprocaprylate and an oil of the formula $R_{15}COOR_{16}$ wherein $R_{15}$ represents a fatty acid residue containing 7 to 19 carbon atoms and $R_{16}$ represents a branched hydrocarbon chain containing 3 to 20 carbon atoms;
  (b) a natural or synthetic essential oil selected from the group consisting of eucalyptus, lavadin, lavender, vetiver, litsea cubeba, lemon, sandalwood, rosemary, camomile, savory, nutmeg, cinnamon, hyssop, caraway, orange, geraniol and cade oils;
  (c) a hydrocarbon selected from the group consisting of hexadecane and paraffin oil;
  (d) a halogenated hydrocarbon selected from the group consisting of perfluorotributylamine, perfluorodecahydronaphthalene, a fluoroester and a fluoroether;
  (e) a silicone selected from the group consisting of a polysiloxane, a polydimethylsiloxane and a fluorosilicone; and
  (f) an ester of an inorganic acid and an alcohol.

15. The composition of claim 1 wherein said aqueous phase in which said amphiphilic lipidic vesicles are dispersed also contains an additive selected from the group consisting of a gelling agent, a polymer, a preservative, a colorant, an opacifying agent, a pH-regulating agent and a perfume.

* * * * *